United States Patent [19]

Krstenansky et al.

[11] Patent Number: 5,279,812

[45] Date of Patent: Jan. 18, 1994

[54] RADIOLABELED ANTICOAGULANT PEPTIDES

[75] Inventors: John L. Krstenansky, Palo Alto, Calif.; Simon J. T. Mao, Loveland, Colo.

[73] Assignee: Merrell Dow Pharmaceuticals Inc., Cincinnati, Ohio

[21] Appl. No.: 676,592

[22] Filed: Mar. 28, 1991

Related U.S. Application Data

[63] Continuation-in-part of Ser. No. 416,335, Oct. 3, 1989, abandoned.

[51] Int. Cl.$^5$ .................... A61K 49/02; C07K 5/00; C07K 7/00
[52] U.S. Cl. .................... 424/1.1; 530/327; 530/328; 530/300
[58] Field of Search ............... 424/1.1; 530/327, 328, 530/300

[56] References Cited

U.S. PATENT DOCUMENTS

| | | | |
|---|---|---|---|
| 4,277,393 | 7/1981 | Sakakibara et al. | 424/1.1 X |
| 4,370,312 | 1/1983 | Jung et al. | 424/1.1 |
| 4,455,290 | 6/1984 | Olexa et al. | 424/1.1 |
| 4,585,740 | 4/1986 | Vanderlaan | 424/1.1 X |
| 4,656,250 | 4/1987 | Morita et al. | 424/1.1 X |
| 4,767,742 | 8/1988 | Dodt et al. | 514/12 |
| 4,791,100 | 12/1988 | Krammer et al. | 514/12 |
| 5,192,747 | 3/1993 | Krstenansky | 514/15 |

FOREIGN PATENT DOCUMENTS

| | | |
|---|---|---|
| 0276014 | 7/1988 | European Pat. Off. |
| 0291981 | 11/1988 | European Pat. Off. |
| 0291982 | 11/1988 | European Pat. Off. |
| 333356 | 9/1989 | European Pat. Off. ...... A61K 37/00 |
| 0347376 | 12/1989 | European Pat. Off. |

OTHER PUBLICATIONS

Krstenansky J. L. et al., Thrombosis and Haemostasis (Stuttgart) 63 (2) 208–214 (1990).
Krstenansky J. L. et al., Thrombosis Research 52; 137–141, (1988).
Chemical Abstracts, vol. 109, 231560t, p. 918,(1988).
Krstenansky J. L. et al., Peptides Chemistry and Biology, Proceed. of 10th American Peptide Sym., May (1987) pp. 447–448.
Krstenansky J. L. et al., J. Med. Chem. 1987, 30, pp. 1688–1691.
Krstenansky, J. L., et al., Thrombosis Research 54, 319–325 (1989).
Cram, D. J., et al., Organic Chemistry, 2nd Edition, McGraw Hill, p. 609(1964).
Owen, T. J., et al., J. Med. Chem., 31, 1009–1011 (1988).
Minar, E., et al., Klin Wochenschr Feb 15;63(4):190–1 (1985) [abstract of].
Markwardt, F., et al., Thromb. Haemostasis, 52(2), 160–3 (1984) [abstract of].
Markwardt, F., et al., Thromb Haemost Jun 28;47(3):226–9 (1982) [abstract of].
Markwardt, F., et al., Thromb Haemost Jun 28;49(3):235–7 (1983) [abstract of].
Bajusz, S., et al., Proc. 18th European Peptide Symposium, 473–476 (1984).
Krstenansky et al., Biochim. Biophys. Acta 957, 53–59 (1988).
Sturzebecher, The Thrombin (R. Machovich, Ed.) vol. 1, 131–160, CRC Press, Boca Roton, Fla. (1984).
Hruby, V., Life Sciences 31, 189–199 (1982).
Mao, S. J. T., et al., Biochemistry 27, 8170–8173 (1988).
Maraganore, J. M., et al., J. Biol. Chem. 264(15), 8692–8698 (1989).

*Primary Examiner*—Robert L. Stoll
*Attorney, Agent, or Firm*—T. Helen Payne; Kenneth J. Collier

[57] ABSTRACT

This invention relates to the usage of anticoagulant peptide derivatives that are iodinated.

16 Claims, No Drawings

SEQUENCE LISTING ( 1 ) GENERAL INFORMATION:

( 1 1 1 ) NUMBER OF SEQUENCES: 27

( 2 ) INFORMATION FOR SQE ID NO:1:

( i ) SEQUENCE CHARACTERISTICS:
      ( A ) LENGTH: 65 amino acids
      ( B ) TYPE: amino acid
      ( D ) TOPOLOGY: linear ( i i ) MOLECULAR TYPE: peptide ( i x ) FEATURE:
      ( A ) NAME/KEY: Modified-site
      ( B ) LOCATION: 63
      ( D ) OTHER INFORMATION: /note="Tyr is O4-sulfotyrosine"

( x ) PUBLICATION INFORMATION:
      ( A ) AUTHORS: DODT, J
                    MULLER, H P
                    SEEMULLER, U
                    CHANG, J Y
      ( C ) JOURNAL: FEBS Lett.
      ( D ) VOLUME: 165
      ( F ) PAGES: 180-183
      ( G ) DATE: 1984

( x ) PUBLICATION INFORMATION:
      ( A ) AUTHORS: PETERSEN, T E
                    ROBERTS, H R
                    SOTTRUP-JENSEN, L
                    MAGNUSSON, S
                    BAGDY, D
      ( C ) JOURNAL: PROTIDES OF THE BIOLOGICAL FLUIDS, PROC. 23RD COLLOQ.
      ( F ) PAGES: 145-149
      ( G ) DATE: 1976

( x ) PUBLICATION INFORMATIONS:
      ( A ) AUTHORS: FOLKERS, PJM
                    CLORE, G M
                    DRISCOLL, P C
                    DODT, J
                    KOEHLER, S ( i x ) SEQUENCE DESCRIPTION: SEQ ID NO:1:

Val Val Tyr Thr Asp Cys Thr Glu Ser Gly Gln Asn Leu Cys Leu Cys
 1            5                    10                   15

Glu Gly Ser Asn Val Cys Gly Gln Gly Asn Lys Cys Ile Leu Gly Ser
             20                 25                  30

Asp Gly Glu Lys Asn Gln Cys Val Thr Gly Glu Gly Thr Pro Lys Pro
         35                 40                 45

Gln Ser His Asn Asp Gly Asp Phe Glu Glu Ile Pro Glu Glu Tyr Leu
     50                 55                 60

Gln
65

( 2 ) INFORMATION FOR SEQ ID NO:2:

( i ) SEQUENCE CHARACTERISTICS:
      ( A ) LENGTH: 66 amino acids
      ( B ) TYPE: amino acid
      ( D ) TOPOLOGY: linear ( i i ) MOLECULE TYPE: peptide ( i x ) FEATURE:
      ( A ) NAME/KEY: Modified-site
      ( B ) LOCATION: 64
      ( D ) OTHER INFORMATION: /not="Tyr is O4-sulfotyrosine"

( x ) PUBLICATION INFORMATION:
    ( A ) AUTHORS: DODT, J
                    MACHLEIDT, W
                    SEEMULLER, U
                    MASCHLER, R
                    FRITZ, H
    ( C ) JOURNAL: Biol. Chem. Hoppe-Seyler
    ( D ) VOLUME: 367
    ( F ) PAGES: 803-811
    ( G ) DATE: 1986

( x i ) SEQUENCE DESCRIPTION: SEQ ID NO:2:

```
Ile Thr Tyr Thr Asp Cys Thr Glu Ser Gly Gln Asn Leu Cys Leu Cys
 1               5                  10                      15

Glu Gly Ser Asn Val Cys Gly Lys Gly Asn Lys Cys Ile Leu Gly Ser
            20                  25                      30

Gln Gly Lys Asp Asn Gln Cys Val Thr Gly Glu Gly Thr Pro Lys Pro
        35              40                  45

Gln Ser His Asn Gln Gly Asp Phe Glu Pro Ile Pro Glu Asp Ala Tyr
    50                      55                  60

Asp Glu
65
```

( 2 ) INFORMATION FOR SEQ ID NO:3:

( i ) SEQUENCE CHARACTERISTICS:
        ( A ) LENGTH: 72 amino acids
        ( B ) TYPE: amino acid
        ( D ) TOPOLOGY: linear ( i i ) MOLECULAR TYPE: peptide ( i x ) FEATURE:
        ( A ) NAME/KEY: Region
        ( B ) LOCATION: 1..7
        ( D ) OTHER INFORMATION: /note="signal sequence 1-7"

( i x ) FEATURE:
        ( A ) NAME/KEY: Region
        ( B ) LOCATION: 8..72
        ( D ) OTHER INFORMATION: /note="Mature Hirudin 8-72"

( i x ) FEATURE:
        ( A ) NAME/KEY: Modified-site
        ( B ) LOCATION: 70
        ( D ) OTHER INFORMATION: /note="Tyr is O4-sulfotyrosine"

( x ) PUBLICATION INFORMATION:
        ( A ) AUTHORS: HARVEY, R P
                    DEGRYSE, E
                    STEFANI, L
                    SCHAMBER, F
                    CAZENZVE, J P
                    COURTNEY, M
                    TOLSTOSHEV, P
                    LECOCQ, J P
        ( C ) JOURNAL: Proc. Natl. Acad. Sci. U.S.A
        ( D ) VOLUME: 83
        ( F ) PAGES: 1084-1088
        ( G ) DATE: 1986

( x i ) SEQUENCE DESCRIPTION: SEQ ID NO:3:

```
Ala Ile Cys Val Ser Gln Ala Ile Thr Tyr Thr Asp Cys Thr Glu Ser
 1               5                  10                      15

Gly Gln Asn Leu Cys Leu Cys Glu Gly Ser Asn Val Cys Gly Lys Gly
            20                  25                      30

Asn Lys Cys Ile Leu Gly Ser Asn Gly Lys Gly Asn Gln Cys Val Thr
        35              40                  45

Gly Glu Gly Thr Pro Asn Pro Glu Ser His Asn Asn Gly Asp Phe Glu
    50                      55                  60

Glu Ile Pro Glu Glu Tyr Leu Gln
```

(2) INFORMATION FOR SEQ ID NO:4:

(i) SEQUENCE CHARACTERISTICS:
        (A) LENGTH: 10 amino acids
        (B) TYPE: amino acid
        (D) TOOPOLOGY: linear (ii) MOLECULE TYPE: peptide (ix) FEATURE:
        (A) NAME/KEY: Modified-site
        (B) LOCATION: 1
        (D) OTHER INFORMATION: /note="Xaa is
            N-alpha-succinyl-3,5-diiodotyrosine
            (Suc-3,5-diI-Tyr)"

(ix) FEATURE:
        (A) NAME/KEY: Modified-site
        (B) LOCATION: 9
        (D) OTHER INFORMATION: /note="Xaa is cyclohexylalanine
            (Cha)"

(ix) FEATURE:
        (A) NAME/KEY: Modified-site
        (B) LOCATION: 10
        (D) OTHER INFORMATION: /note="Xaa is a D-glutamic acid
            (D-Glu)"

(xi) SEQUENCE DESCRIPTION: SEQ ID NO:4:

Xaa Glu Pro Ile Pro Glu Glu Ala Xaa Xaa
1                5

(2) INFORMATION FOR SEQ ID NO:5:

(i) SEQUENCE CHARACTERISTICS:
        (A) LENGTH: 10 amino acids
        (B) TYPE: amino acid
        (D) TOPOLOGY: linear (ii) MOLECULAR TYPE: peptide (ix) FEATURE:
        (A) NAME/KEY: Modified-site
        (B) LOCATION: 1
        (D) OTHER INFORMATION: /note="Xaa is
            N-alpha-succinyl-3,5-[ditritium]-tyrosine
            (Suc-3,5-di[3H]-Tyr) or"

(ix) FEATURE:
        (A) NAME/KEY: Modified-site
        (B) LOCATION: 1
        (D) OTHER INFORMATION: /note="(cont'd)
            N-alpha-succinyl-3-[tritium]-tyrosine
            (Suc-3-[tritium]-Tyr)(Suc-[3H]-Tyr)"

(ix) FEATURE:
        (A) NAME/KEY: Modified-site
        (B) LOCATION: 9
        (D) OTHER INFORMATION: /note="Xaa is cyclohexylalanine
            (Cha)"

(ix) FEATURE:
        (A) NAME/KEY: Modified-site
        (B) LOCATION: 10
        (D) OTHER INFORMATION: /note="Xaa is D-glutamic acid
            (D-Glu)"

(ix) SEQUENCE DESCRIPTION: SEQ ID NO:5:

Xaa Glu Pro Ile Pro Glu Glu Ala Xaa Xaa
1                5                          10

(2) INFORMATION FOR SEQ ID NO:6:

(i) SEQUENCE CHARACTERISTICS:
        (A) LENGTH: 11 amino acids

-continued

```
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note="Xaa is
            N-alpha-succinyl-3,5-diiodotyrosine
            (Suc-3,5-diI-Tyr)"

(ix) FEATURE:
        (A) NAME/KEY: Modified-site
        (B) LOCATION: 2
        (D) OTHER INFORMATION: /note="Xaa is 3,5-diiodotyrosine
            (3,5-diI-Tyr)"

(ix) FEATURE:
        (A) NAME/KEY: Modified-site
        (B) LOCATION: 10
        (D) OTHER INFORMATION: /note="Xaa is cyclohexylalanine
            (Cha)"

(ix) FEATURE:
        (A) NAME/KEY: Modified-site
        (B) LOCATION: 11
        (D) OTHER INFORMATION: /note="Xaa is D-glutamic acid
            (D-Glu)"

(ix) SEQUENCE DESCRIPTION: SEQ ID NO:6:

Xaa Xaa Glu Pro Ile Pro Glu Glu Ala Xaa Xaa
1               5                   10

(2) INFORMATION FOR SEQ ID NO:7:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note="Xaa is
            N-alpha-succinyl-tyrosine (Suc-Tyr)"

(ix) FEATURE:
        (A) NAME/KEY: Modified-site
        (B) LOCATION: 8
        (D) OTHER INFORMATION: /note="Xaa is cyclohexylalanine
            (Cha)"

(ix) FEATURE:
        (A) NAME/KEY: Modified-site
        (B) LOCATION: 9
        (D) OTHER INFORMATION: /note="Xaa is D-glutamic acid
            (D-Glu)"

Xaa Pro Ile Pro Glu Glu Ala Xaa Xaa
1               5

(2) INFORMATION FOR SEQ ID NO:8:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO:8:

Gly Asp Phe Glu Glu Ile Glu Glu Tyr Leu Gln
1               5                   10
```

( 2 ) INFORMATION FOR SEQ ID NO:9:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="Xaa is
            N-alpha-succinyl-tyrosine (Suc-Tyr)"

( i x ) FEATURE:
        ( A ) NAME/KEY: Modified-site
        ( B ) LOCATION: 4
        ( D ) OTHER INFORMATION: /note="Xaa is
            tetrahydroisoquinoline 3-carboxylate (Tiq)"

( i x ) FEATURE:
        ( A ) NAME/KEY: Modified-site
        ( B ) LOCATION: 8
        ( D ) OTHER INFORMATION: /note="Xaa is cyclohexylalanine
            ( C h a )"

( i x ) FEATURE:
        ( A ) NAME/KEY: Modified-site
        ( B ) LOCATION: 9
        ( D ) OTHER INFORMATION: /note="Xaa is D-glutamic acid
            ( D - G l u )"

( x i ) SEQUENCE DESCRIPTION: SEQ ID NO:9:

Xaa Glu Pro Xaa Glu Glu Ala Xaa Xaa
1                 5

( 2 ) INFORMATION FOR SEQ ID NO:10:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) OTHER INFORMATION: /note="Xaa is
            N-alpha-succinyl-tyrosine (Suc-Tyr)"

( i x ) FEATURE:
        ( A ) NAME/KEY: Modified-site
        ( B ) LOCATION: 9
        ( D ) OTHER INFORMATION: /note="Xaa is glutamin-1-amide
            ( G l n - N H 2 )"

( x i ) SEQUENCE DESCRIPTION: SEQ ID NO:10:

Xaa Glu Pro Ile Pro Glu Glu Ala Xaa
1                 5

( 2 ) INFORMATION FOR SEQ ID NO:11:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="Xaa is
            N-alpha-succinyl-tyrosine (Suc-Tyr)"

( i x ) FEATURE:
        ( A ) NAME/KEY: Modified-site (B) LOCATION: 8
(D) OTHER INFORMATION: /note="Xaa is cyclohexylalanine (Cha)"

(ix) FEATURE:
  (A) NAME/KEY: Modified-site
  (B) LOCATION: 9
  (D) OTHER INFORMATION: /note="Xaa is glutamin-1-amide (Gln-NH2)"

(ix) SEQUENCE DESCRIPTION: SEQ ID NO:11:

Xaa Glu Pro Ile Pro Glu Glu Xaa Xaa
1               5

(2) INFORMATION FOR SEQ ID NO:12:

(i) SEQUENCE CHARACTERISTICS:
    (A) LENGTH: 9 amino acids
    (B) TYPE: amino acid
    (D) TOPOLOGY: linear (ii) MOLECULE TYPE: peptide (ix) FEATURE:
    (A) NAME/KEY: Modified-site
    (B) LOCATION: 1
    (D) OTHER INFORMATION: /note="Xaa is N-alpha-succinyl-tyrosine (Suc-Tyr)"

(ix) FEATURE:
    (A) NAME/KEY: Modified-site
    (B) LOCATION: 8
    (D) OTHER INFORMATION: /note="Xaa is cyclohexylalanine (Cha)"

(xi) SEQUENCE DESCRIPTION: SEQ ID NO:12:

Xaa Glu Pro Ile Pro Glu Ala Xaa Asn
1               5

(2) INFORMATION FOR SEQ ID NO:13:

(i) SEQUENCE CHARACTERISTICS:
    (A) LENGTH: 9 amino acids
    (B) TYPE: amino acid
    (D) TOPOLOGY: linear (ii) MOLECULE TYPE: peptide (ix) FEATURE:
    (A) NAME/KEY: Modified-site
    (B) LOCATION: 1
    (D) OTHER INFORMATION: /note="Xaa is N-alpha-succinyl-tyrosine (Suc-Tyr)"

(ix) SEQUENCE DESCRIPTION: SEQ ID NO:13:

Xaa Glu Pro Ile Pro Glu Glu Ala Asn
1               5

(2) INFORMATION FOR SEQ ID NO:14:

(i) SEQUENCE CHARACTERISTICS:
    (A) LENGTH: 9 amino acids
    (B) TYPE: amino acid
    (D) TOPOLOGY: linear (ii) MOLECULE TYPE: peptide (ix) FEATURE:
    (A) NAME/KEY: Modified-site
    (B) LOCATION: 1
    (D) OTHER INFORMATION: /note="Xaa is N-alpha-maleyl-tyrosine (Mal-Tyr)"

(ix) FEATURE:
    (A) NAME/KEY: Modified-site
    (B) LOCATION: 8

( D ) OTHER INFORMATION: /note="Xaa is cyclohexylalanine
                        ( C h a )"

( i x ) FEATURE:
                    ( A ) NAME/KEY: Modified-site
                    ( B ) LOCATION: 9
                    ( D ) OTHER INFORMATION: /note="Xaa is D-glutamic acid
                        ( D - G l u )"

( x i ) SEQUENCE DESCRIPTION: SEQ ID NO:14:

Xaa Pro Ile Pro Glu Glu Ala Xaa Xaa
1                   5

( 2 ) INFORMATION FOR SEQ ID NO:15:

( i ) SEQUENCE CHARACTERISTICS:
                    ( A ) LENGTH: 9 amino acids
                    ( B ) TYPE: amino acid
                    ( D ) TOPOLOGY: linear ( i i ) MOLECULE TYPE: peptide ( i x ) FEATURE:
                    ( A ) NAME/KEY: Modified-site
                    ( B ) LOCATION: 1
                    ( D ) OTHER INFORMATION: /note="Xaa is
                        N-alpha-succinyl-beta-(naphthyl)alanine (Suc-Nap)"

( i x ) FEATURE:
                    ( A ) NAME/KEY: Modified-site
                    ( B ) LOCATION: 8
                    ( D ) OTHER INFORMATION: /note="Xaa is cyclohexylalanine
                        ( C h a )"

( i x ) FEATURE:
                    ( A ) NAME/KEY: Modified-site
                    ( B ) LOCATION: 9
                    ( D ) OTHER INFORMATION: /note="Xaa is D-glutamic acid
                        ( D - G l u )"

( i x ) SEQUENCE DESCRIPTION: SEQ ID NO:15:

Xaa Pro Ile Pro Glu Glu Ala Xaa Xaa
1                   5

( 2 ) INFORMATION FOR SEQ ID NO:16:

( i ) SEQUENCE CHARACTERISTICS:
                    ( A ) LENGTH: 9 amino acids
                    ( B ) TYPE: amino acid
                    ( D ) TOPOLOGY: linear ( i i ) MOLECULE TYPE: peptide ( i x ) FEATURE:
                    ( A ) NAME/KEY: Modified-site
                    ( B ) LOCATION: 1
                    ( D ) OTHER INFORMATION: /note="Xaa is
                        N-alpha-succinyl-tyrosine (Suc-Tyr)"

( i x ) FEATURE:
                    ( A ) NAME/KEY: Modified-site
                    ( B ) LOCATION: 8
                    ( D ) OTHER INFORMATION: /note="Xaa is cyclohexylalanine
                        ( C h a )"

( i x ) FEATURE:
                    ( A ) NAME/KEY: Modified-site
                    ( B ) LOCATION: 9
                    ( D ) OTHER INFORMATION: /note="Xaa is D-glutamic acid
                        ( D - G l u )"

( x i ) SEQUENCE DESCRIPTION: SEQ ID NO:16:

Xaa Glu Ile Pro Glu Glu Ala Xaa Xaa
1                   5

( 2 ) INFORMATION FOR SEQ ID NO:17:

( i ) SEQUENCE CHARACTERISTICS:
    ( A ) LENGTH: 9 amino acids
    ( B ) TYPE: amino acid
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note="Xaa is
        N-alpha-succinyl-tyrosine (Suc-Tyr)"

( i x ) FEATURE:
    ( A ) NAME/KEY: Modified-site
    ( B ) LOCATION: 8
    ( D ) OTHER INFORMATION: /note="Xaa is cyclohexylalanine
        ( C h a )"

( i x ) FEATURE:
    ( A ) NAME/KEY: Modified-site
    ( B ) LOCATION: 9
    ( D ) OTHER INFORMATION: /note="Xaa is D-glutamic acid
        ( D - G l u )"

( x i ) SEQUENCE DESCRIPTION: SEQ ID NO:17:

Xaa  Glu  Pro  Pro  Glu  Glu  Ala  Xaa  Xaa
1                       5

( 2 ) INFORMATION FOR SEQ ID NO:18:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="Xaa is
            N-alpha-succinyl-tyrosine (Suc-Tyr)"

( i x ) FEATURE:
        ( A ) NAME/KEY: Modified-site
        ( B ) LOCATION: 8
        ( D ) OTHER INFORMATION: /note="Xaa is cyclohexylalanine
            ( C h a )"

( i x ) FEATURE:
        ( A ) NAME/KEY: Modified-site
        ( B ) LOCATION: 9
        ( D ) OTHER INFORMATION: /note="Xaa is D-glutamic acid
            ( D - G l u )"

( x i ) SEQUENCE DESCRIPTION: SEQ ID NO:18:

Xaa  Glu  Pro  Ile  Glu  Glu  Ala  Xaa  Xaa
1                       5

( 2 ) INFORMATION FOR SEQ ID NO:19:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="Xaa is
            N-alpha-succinyl-tyrosine (Suc-Tyr)"

( i x ) FEATURE:
        ( A ) NAME/KEY: Modified-site

-continued (B) LOCATION: 8
            (D) OTHER INFORMATION: /note="Xaa is cyclohexylalanine
                (Cha)"

(ix) FEATURE:
            (A) NAME/KEY: Modified-site
            (B) LOCATION: 9
            (D) OTHER INFORMATION: /note="Xaa is D-glutamic acid
                (D-Glu)"

(xi) SEQUENCE DESCRIPTION: SEQ ID NO:19:

Xaa Glu Pro Ile Pro Glu Ala Xaa Xaa
1                 5

(2) INFORMATION FOR SEQ ID NO:20:

(i) SEQUENCE CHARACTERISTICS:
            (A) LENGTH: 9 amino acids
            (B) TYPE: amino acid
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /note="Xaa Is
                N-alpha-succinyl-tyrosine (Suc-Tyr)"

(ix) FEATURE:
            (A) NAME/KEY: Modified-site
            (B) LOCATION: 9
            (D) OTHER INFORMATION: /note="Xaa is D-glutamic acid
                (D-Glu)"

(xi) SEQUENCE DESCRIPTION: SEQ ID NO:20:

Xaa Glu Pro Ile Pro Glu Glu Ala Xaa
1                 5

(2) INFORMATION FOR SEQ ID NO:21:

(i) SEQUENCE CHARACTERISTICS:
            (A) LENGTH: 9 amino acids
            (B) TYPE: amino acid
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /note="Xaa is
                N-alpha-succinyl-tyrosine (Suc-Tyr)"

(ix) FEATURE:
            (A) NAME/KEY: Modified-site
            (B) LOCATION: 8
            (D) OTHER INFORMATION: /note="Xaa is cyclohexylalanine
                (Cha)"

(ix) FEATURE:
            (A) NAME/KEY: Modified-site
            (B) LOCATION: 9
            (D) OTHER INFORMATION: /note="Xaa is D-glutamic acid
                (D-Glu)"

(xi) SEQUENCE DESCRIPTION: SEQ ID NO:21:

Xaa Glu Pro Ile Pro Glu Glu Xaa Xaa
1                 5

(2) INFORMATION FOR SEQ ID NO:22:

(i) SEQUENCE CHARACTERISTICS:
            (A) LENGTH: 9 amino acids
            (B) TYPE: amino acid
            (D) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note="Xaa is
        N-alpha-succinyl-tyrosine (Suc-Tyr)"

( x i ) SEQUENCE DESCRIPTION: SEQ ID NO:22:

Xaa Glu Pro Ile Pro Glu Glu Ala Gln
1               5

( 2 ) INFORMATION FOR SEQ ID NO:23:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="Xaa is
            N-alpha-succinyl-phenylalanine (Suc-Phe)"

( i x ) FEATURE:
        ( A ) NAME/KEY: Modified-site
        ( B ) LOCATION: 9
        ( D ) OTHER INFORMATION: /note="Xaa is glutamin-1-amide
            ( Gln-NH2 )"

( x i ) SEQUENCE DESCRIPTION: SEQ ID NO:23:

Xaa Glu Pro Ile Pro Glu Glu Ala Xaa
1               5

( 2 ) INFORMATION FOR SEQ ID NO:24:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="Xaa is
            N-alpha-succinyl-tyrosine (Suc-Tyr)"

( i x ) FEATURE:
        ( A ) NAME/KEY: Modified-site
        ( B ) LOCATION: 9
        ( D ) OTHER INFORMATION: /note="Xaa is cyclohexylalanine
            ( Cha )"

( x i ) SEQUENCE DESCRIPTION: SEQ ID NO:24:

Xaa Glu Pro Ile Pro Glu Glu Ala Xaa
1               5

( 2 ) INFORMATION FOR SEQ ID NO:25:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="Xaa is N-alpha-succinyl-glutamic acid (Suc-Glu)"

( i x ) FEATURE:
  ( A ) NAME/KEY: Modified-site
  ( B ) LOCATION: 8
  ( D ) OTHER INFORMATION: /note="Xaa is cyclohexylalanine
    ( C h a )"

( i x ) FEATURE:
  ( A ) NAME/KEY: Modified-site
  ( B ) LOCATION: 9
  ( D ) OTHER INFORMATION: /note="Xaa is D-glutamic acid
    ( D - G l u )"

( x i ) SEQUENCE DESCRIPTION: SEQ ID NO:25:

Xaa Pro Ile Pro Glu Glu Ala Xaa Xaa
1       5

( 2 ) INFORMATION FOR SEQ ID NO:26:

( i ) SEQUENCE CHARACTERISTICS:
   ( A ) LENGTH: 10 amino acids
   ( B ) TYPE: amino acid
   ( D ) TOPOLOGY: linear ( i i ) MOLECULE TYPE: peptide ( i x ) FEATURE:
   ( A ) NAME/KEY: Modified-site
   ( B ) LOCATION: 1
   ( D ) OTHER INFORMATION: /note="Xaa is a sequence of 1-11
    amino acids of hirudin(ID#Microsoft Corp
    hirudin(ID#Microsoft Corp ( i x ) FEATURE:
   ( A ) NAME/KEY: Modified-site
   ( B ) LOCATION: 1
   ( D ) OTHER INFORMATION: /note="(cont'd) said sequence has
    an amino terminal substituent selected from
    hydrogen, one or two alkyl groups of from 1 to 10"

( i x ) FEATURE:
   ( A ) NAME/KEY: Modified-site
   ( B ) LOCATION: 1
   ( D ) OTHER INFORMATION: /note="(cont'd) carbon atoms, one
    or two acyl groups of from 2 to 10 carbon atoms,
    carbobenzyloxy or t-butyloxy carbonyl"

( i x ) FEATURE:
   ( A ) NAME/KEY: Modified-site
   ( B ) LOCATION: 2
   ( D ) OTHER INFORMATION: /note="Xaa is one to five residues
    of [3H]-Tyr, [125I]-Tyr, [131I]=Tyr, unless A9
    contains a radio-labeled amino acid then"

( i x ) FEATURE:
   ( A ) NAME/KEY: Modified-site
   ( B ) LOCATION: 2
   ( D ) OTHER INFORMATION: /note="(cont'd) A2 can
    additionally be I-Tyr, Tyr, or a bond"

( i x ) FEATURE:
   ( A ) NAME/KEY: Modified-site
   ( B ) LOCATION: 3
   ( D ) OTHER INFORMATION: /note="Xaa is a bond, Glu, or Asp"

( i x ) FEATURE:
   ( A ) NAME/KEY: Modified-site
   ( B ) LOCATION: 4
   ( D ) OTHER INFORMATION: /note="Xaa is a bond, Pro, or Glu"

( i x ) FEATURE:
   ( A ) NAME/KEY: Modified-site
   ( B ) LOCATION: 5
   ( D ) OTHER INFORMATION: /note="Xaa is a bond, or Ile"

( i x ) FEATURE:
   ( A ) NAME/KEY: Modified-site
   ( B ) LOCATION: 6
   ( D ) OTHER INFORMATION: /note="Xaa is a bond, Tiq, Pro, Hyp, 3,4-dihydroPro, thiazolidine-4-carboxylate,
Sar, NMePgl, Azt, or Pip"

( i x ) FEATURE:
  ( A ) NAME/KEY: Modified-site
  ( B ) LOCATION: 7
  ( D ) OTHER INFORMATION: /note = "Xaa is a bond, Glu, or Asp"

( i x ) FEATURE:
  ( A ) NAME/KEY: Modifed-site
  ( B ) LOCATION: 8
  ( D ) OTHER INFORMATION: /note = "Xaa is a bond, Glu, Asp, or
       Ala"

( i x ) FEATURE:
  ( A ) NAME/KEY: Modified-site
  ( B ) LOCATION: 9
  ( D ) OTHER INFORMATION: /note = "Xaa is a lipophilic amino
       acid selected from Tyr, I-Tyr, [125I]-Tyr,
       [ 131I]-Tyr, [3H]-Tyr, Met, Trp, Phe, Leu, Nle"

( i x ) FEATURE:
  ( A ) NAME/KEY: Modified-site
  ( B ) LOCATION: 9
  ( D ) OTHER INFORMATION: /note = "(cont'd) Ile, Val, Cha and
       Pro or is a dipeptide containing at least one of
       these amino acids and an amino acid found in "

( i x ) FEATURE:
  ( A ) NAME/KEY: Modified-site
  ( B ) LOCATION: 9
  ( D ) OTHER INFORMATION: /note = "(cont'd) hirudin (ID#Microsoft Corp
       natural variants of hirudin (ID#Microsoft Corp ( i x ) FEATURE:
  ( A ) NAME/KEY: Modified-site
  ( B ) LOCATION: 10
  ( D ) OTHER INFORMATION: /note = "Xaa is a sequence of 1-11
       amino acids of hirudin (ID#Microsoft Corp
       hirudin (ID#Microsoft Corp ( i x ) FEATURE:
  ( A ) NAME/KEY: Modified-site
  ( B ) LOCATION: 10
  ( D ) OTHER INFORMATION: /note = "(cont'd) or a bond: wherein
       said sequence has a carbonyl substituent (-CO-) of
       the terinal amino acid selected from OH, (C1-C8)"

( i x ) FEATURE:
  ( A ) NAME/KEY: Modified-site
  ( B ) LOCATION: 10
  ( D ) OTHER INFORMATION: /note = "(cont'd) alkoxy, amino, or
       a mono or di (C1-C4) alkyl substituted amino
       group; on the terminal substituent"

( i x ) FEATURE:
  ( A ) NAME/KEY: Modified-site
  ( B ) LOCATION: 10
  ( D ) OTHER INFORMATION: /note = "(cont'd) to the alpha
       carbon of the amino acid is an alcohol (-CH2OH)
       with the proviso that at least 3 elements of"

( i x ) FEATURE:
  ( A ) NAME/KEY: Modified-site
  ( B ) LOCATION: 10
  ( D ) OTHER INFORMATION: /note = "(cont'd) formula 1
       corresponds to amino acids present in hirudin
       ( I D # 1 ) or its variants (ID#Microsoft Corp ( i x ) SEQUENCE DESCRIPTION: SEQ ID NO:26:

Xaa Xaa Xaa Xaa Xaa Xaa Xaa Xaa Xaa Xaa
1               5                   10

( 2 ) INFORMATION FOR SEQ ID NO:27:

( i ) SEQUENCE CHARACTERISTICS:
    ( A ) LENGTH: 10 amino acids
    ( B ) TYPE: amino acid
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note="Xaa is sequence of hirudin
        or its natural variants or portions thereof, a
        bond, or is a peptide containing "

( i x ) FEATURE:
    ( A ) NAME/KEY: Modified-site
    ( B ) LOCATION: 1
    ( D ) OTHER INFORMATION: /note="(cont'd) from 1 to 11
        residues of any amino acid; wherein said sequence
        has an amino terminal residue selected from"

( i x ) FEATURE:
    ( A ) NAME/KEY: Modified-site
    ( B ) LOCATION: 1
    ( D ) OTHER INFORMATION: /note="(cont'd) hydrogen, one or
        two alkyl groups of from 1 to 10 carbons atoms, one
        or two acyl groups of from 2 to 10 carbons"

( i x ) FEATURE:
    ( A ) NAME/KEY: Modified-site
    ( B ) LOCATION: 1
    ( D ) OTHER INFORMATION: /note="(cont'd) atoms,
        carbobenzyloxy or t-butyloxy carbonyl"

( i x ) FEATURE:
    ( A ) NAME/KEY: Modified-site
    ( B ) LOCATION: 2
    ( D ) OTHER INFORMATION: /note="Xaa is zero to five
        residues of I-Tyr, [3H-]Tyr, [125I]-Tyr,
        [ 131I]-Tyr, or L-aromatic amino acid"

( i x ) FEATURE:
    ( A ) NAME/KEY: Modified-site
    ( B ) LOCATION: 2
    ( D ) OTHER INFORMATION: /note="(cont'd) if A9 contains a
        radiolabeled amino acid"

( i x ) FEATURE:
    ( A ) NAME/KEY: Modified-site
    ( B ) LOCATION: 3
    ( D ) OTHER INFORMATION: /note="Xaa is Glu, Asp, or Ala"

( i x ) FEATURE:
    ( A ) NAME/KEY: Modified-site
    ( B ) LOCATION: 4
    ( D ) OTHER INFORMATION: /note="Xaa is any amino acid"

( i x ) FEATURE:
    ( A ) NAME/KEY: Modified-site
    ( B ) LOCATION: 5
    ( D ) OTHER INFORMATION: /note="Xaa is Ile, Val, Leu, Nle,
        Ala, or Phe"

( i x ) FEATURE:
    ( A ) NAME/KEY: Modified-site
    ( B ) LOCATION: 6
    ( D ) OTHER INFORMATION: /note="Xaa is Pro, Hyp, Azt, Pip,
        DhPro, thiazolidine-4-carboxylate, Sar NMePgl or
        D-Ala"

( i x ) FEATURE:
    ( A ) NAME/KEY: Modified-site
    ( B ) LOCATION: 7
    ( D ) OTHER INFORMATION: /note="Xaa is any amino acid"

( i x ) FEATURE:
    ( A ) NAME/KEY: Modified-site
    ( B ) LOCATION: 8
    ( D ) OTHER INFORMATION: /note="Xaa is any amino acid"

( i x ) FEATURE:
    ( A ) NAME/KEY: Modified-site
    ( B ) LOCATION: 9
    ( D ) OTHER INFORMATION: /note="Xaa is a lipophilic amino
        acid selected from Tyr, I-Tyr, [131I]-Tyr,
        [ 125I]-Tyr, [3H]-Tyr, Met, Trp, Phe,"

(ix) FEATURE:
 (A) NAME/KEY: Modified-site
 (B) LOCATION: 9
 (D) OTHER INFORMATION: /note="(cont'd) Leu, Nle, Ile, Val, Cha, His, Ala and Pro or is a dipeptide containing at least one of these amino"

(ix) FEATURE:
 (A) NAME/KEY: Modified-site
 (B) LOCATION: 9
 (D) OTHER INFORMATION: /note="(cont'd) acid or any lipophilic amino acids"

(ix) FEATURE:
 (A) NAME/KEY: Modified-site
 (B) LOCATION: 10
 (D) OTHER INFORMATION: /note="Xaa is sequences of hirudin or its natural variants or portions thereof, a bond, or is a peptide containing"

(ix) FEATURE:
 (A) NAME/KEY: Modified-site
 (B) LOCATION: 10
 (D) OTHER INFORMATION: /note="(cont'd) from 1 to 11 residues of any amino acid; wherein said sequence has a carboxy terminal residue selected from"

(ix) FEATURE:
 (A) NAME/KEY: Modified-site
 (B) LOCATION: 10
 (D) OTHER INFORMATION: /note="(cont'd) OH, (C1-C8) alkoxy, amino, or mon or di (C1-C4) alkyl substituted amin acids"

(i) SEQUENCE DESCRIPTION: SEQ ID NO:27:

Xaa Xaa Xaa Xaa Xaa Xaa Xaa Xaa Xaa Xaa
1               5                   10

1

RADIOLABELED ANTICOAGULANT PEPTIDES

FIELD OF INVENTION

This is a continuation-in-part of U.S. Ser. No. 416,335 filed Oct. 3, 1989 now abandoned.

This invention relates to novel anticoagulant peptides capable of being radio-labeled and as such are valuable reagents for the detection of thrombin within the body or appropriate samples thereof as a diagnostic kit.

BACKGROUND OF INVENTION

Anticoagulants are useful therapeutic agents in the pharmacological treatment of, for example, acute deep venous thrombosis, pulmonary embolism, acute arterial embolization of the extremities, myocardial infarction, and disseminated intravascular coagulation. Prophylactic administration of anticoagulants is believed to prevent a recurrence of embolism in patients with rheumatic or arteriosclerotic heart disease and to prevent certain thromboembolic complications of surgery. Administration of anticoagulants has also been indicated in the treatment of coronary artery and cerebrovascular disease. Arterial thrombosis, particularly in arteries supplying the heart muscle and brain, is a leading cause of death.

Hirudin is a 65 amino acid residue polypeptide isolated from the salivary glands of leeches. It is a thrombin specific inhibitor and therefore can be used as an anticoagulant agent. Although quite potent, clinical use of hirudin isolated from leech extracts seems unlikely because of its limited quantity, expense, and allergic reactions which commonly follow administration of any foreign protein of this size.

Originally, applicants discovered a specific region of hirudin that is responsible, at least in part, for its anticoagulant activity. The peptide region (amino acid residues 55 to 65 of hirudin) was chemically synthesized and shown to bind the recognition site of thrombin; the recognition site being spatially distinct from the the enzymatic cleavage site. Binding of synthetic peptides were also shown to competitively prevent binding of fibrinogen to the recognition site of thrombin, an important prerequisite to fibrin production and clot formation, and are thereby of potential medical value as anticoagulants.

Applicants have now prepared certain iodotyrosine, and radioisotopically labeled tyrosine derivatives of this peptide. The present invention provides a method for labeling hirudin peptides while preserving the binding site activity present. The iodotyrosine peptides and radio-isotope derivatives in this invention also maintain their parental attributes as anticoagulants, and thus may also allow for a scientifically interesting and therapeutically significant adjuncts. Specifically, the ability to incorporate radioactive isotopes of hydrogen and iodine into the peptide and maintain biological activity of the peptide provides a new important reagent in pharmaceutical testing and usage of anticoagulants. Such reagents would be expected to be important in animal and biochemical studies i.e., radioimmuneassays, screening of drug agonists and antagonists, pharmacokinetic and biodistribution studies, and diagnostic imaging. Moreover, the presence of the iodotyrosine or radio-isotopes thereof, may prove of value in drug development and testing of antithrombotic agents and such derivatives may in themselves have enhanced potency and extended duration of action.

SUMMARY OF THE INVENTION

Peptide derivatives of the formula (ID#27)

$X-A_1-A_2-A_3-A_4-A_5-A_6-A_7-A_8-A_9-A_{10}-Y$ wherein;

X is an amino terminal residue selected from hydrogen, one or two alkyl groups of from 1 to 10 carbon atoms, one or two acyl groups of from 2 to 10 carbon atoms, carbobenzyloxy or t-butyloxy carbonyl;

$A_1$ is sequences of hirudin or its natural variants or portions thereof, a bond, or is a peptide containing from 1 to 11 residues of any amino acid;

$A_2$ is zero to five residues of I-Tyr, [$^3$H-]Tyr, [$^{125}$I]-Tyr, [$^{131}$I]-Tyr, or L-aromatic amino acid if $A_9$ contains a radiolabeled amino acid;

$A_3$ is Glu, Asp, Ala;

$A_4$ is any amino acid;

$A_5$ is Ile, Val, Leu, Nle, Ala, or Phe;

$A_6$ is Pro, Hyp, Azt, Pip, DhPro, thiazolidine-4-carboxylate, Sar, NMePgl or D-Ala;

$A_7$ is any amino acid;

$A_8$ is any amino acid;

$A_9$ is a lipophilic amino acid selected from Tyr, I-Tyr, [$^{131}$I]-Tyr, [$^{125}$I]-Tyr, [$^3$H]-Tyr, Met, Trp, Phe, Leu, Nle, Ile, Val, Cha, His, Ala and pro or is a dipeptide containing at least one of these amino acids or any lipophilic amino acids;

$A_{10}$ is sequences of hirudin or its natural variants or portions thereof, a bond, or is a peptide containing from 1 to 11 residues of any amino acid;

Y is a carboxy terminal residue selected from OH, ($C_1$-$C_8$) alkoxy, amino, or mono Or di ($C_1$-$C_4$) alkyl substituted amino acids;

as anticoagulant agents, are useful for diagnostic imaging, for diagnostic detection and quantification in a "kit", or as an anticoagulant agent, and at least one substituent contains a radioisotope.

DETAILED DESCRIPTION OF THE INVENTION

The following common abbreviations of; (1) amino acids and their three letter code, (2) modified and unusual amino acids, and (3) terminal amino and carboxy substituents used throughout this specification:

| (1): THE AMINO ACIDS AND THEIR THREE LETTER CODE | |
|---|---|
| L-AMINO ACIDS | D-AMINO ACIDS |
| Ala - alanine | D-Ala - D-alanine |
| Arg - arginine | D-Arg - D-arginine |
| Asn - asparagine | D-Asn - D-asparagine |
| Asp - aspartic acid | D-Asp - D-aspartic acid |
| Cys - cysteine | D-Cys - D-cysteine |
| Gly - glycine | |
| Glu - glutamic acid | D-Glu - D-glutamic acid |
| Val - valine | D-Val - D-valine |
| Gln - glutamine | D-Gln - D-glutamine |
| His - histidine | D-His - D-histidine |
| Ile - isoleucine | D-Ile - D-isoleucine |
| Leu - leucine | D-Leu - D-leucine |
| Lys - lysine | D-Lys - D-lysine |
| Phe - phenylalanine | D-Phe - D-phenylalanine |

-continued

| | |
|---|---|
| Met - methionine | D-Met - D-methionine |
| Pro - proline | D-Pro - D-proline |
| Ser - serine | D-Ser - D-serine |
| Thr - threonine | D-Thr - D-threonine |
| Trp - tryptophan | D-Trp - D-tryptophan |
| Tyr - tyrosine | D-Tyr - D-tyrosine |

(2): MODIFIED AND UNUSUAL AMINO ACIDS

Aba - α-amino-n-butyric acid
pClPhe - para-chloro-phenylalanine
Cha - cyclohexylalanine
Chg - cyclohexylglycine
Hyp - hydroxyproline I-Tyr - 3-idodotyrosine (3-I-Tyr), 5-iodotyrosine
(5-I-Tyr), 3,5-diiodotyrosine (3,5-diI-Tyr).
[$^3$H]-Tyr - [3-$^3$H]-tyrosine([3-$^3$H]-Tyr), [5-$^3$H]-tyrosine
([5-$^3$H]-Tyr), [3,5-di$^3$H]-tyrosine ([3,5-di$^3$H]-Tyr).
[125I]-Tyr - [5-$^{125}$I]-iodotyrosine ([5-$^{125}$I]-Tyr), [3-$^{125}$I]-iodotyrosine ([3-$^{125}$I]-Tyr), [3,5-di$^{125}$I]-diiodotyrosine ([3,5-di$^{125}$I]-Tyr).
[$^{131}$I]-Tyr - [3-$^{131}$I]-Tyrosine ([3-$^{131}$I]-Tyr), [5-$^{131}$I]-Tyrosine ([5-$^{131}$I]-Tyr), [3,5-di$^{131}$I]-Tyrosine ([3,5-di$^{131}$I]-Tyr).
3,5-diI-Tyr - 3,5,-diiodotyrosine
γMeGlu - D-glutamic acid gamma methyl ester
NMePhe - N-methyl phenylalanine
NMePgl - N-methyl phenylglycine
Npa - β-(naphthyl)alanine
DhPro - 3,4-dihydroproline
pNO$_2$Phe - para-nitro-phenylalanine
pCPhe - para-cloro-phenylalanine
Nle - norleucine
Orn - ornithine
Pip - pipecolate
Pba - p-aminophenyl butyric acid
pSubPhe - para substituted phenylalanine
Pgl - phenylglycine
Sar - sarcosine (N-methylglycine)
SubPhe - ortho, meta, or para, mono- or di- substituted phenylalanine
Tha - β-(2-thienyl)-alanine
Tiq - Tetrahydroisoquinoline 3-carboxylate

AMINO AND CARBOXY TERMINAL ACID SUSTITUENTS

Ac - acetyl
Azt - azetidine-2-carboxylate
Cin - cinnamoyl
DhCin - 3,4-dihydrocinnamoyl
Glt - glutaryl
Mal - maleyl
Oac - 8-aminooctanoic acid -continued Oct - n-octyl
Suc - succinyl
Glt - glutaryl
Tfa - trifloroacetyl
- C-terminal amide The following designates a sequence listing of the known naturally occurring amino acid sequence variations of hirudin. The independent sequence listings are further described and setforth in the sequence listing section of the application SEQUENCE LISTING OF
AMINO ACID SEQUENCE VARIATIONS
FOUND IN DIFFERENT POSITIONS OF HIRUDIN
(see sequence identification section for independent listings)

```
 1                   5                  10                  15
Val Val Tyr Thr Asp Cys Thr Glu Ser Gly Gln Asn Leu Cys Leu
Ile Thr 20                  25                  30
Cys Glu Gly Ser Asn Val Cys Gly Gln Gly Asn Lys Cys Ile Leu
                                    Lys 35                  40                  45
Gly Ser Asp Gly Glu Lys Asn Gln Cys Val Thr Gly Glu Gly Thr
            Asn     Lys Gly
            Gln         Asp 50                  55                  60
Pro Lys Pro Gln Ser His Asn Asp Gly Asp Phe Glu Glu Ile Pro
    Asn         Glu         Asn
                            Gln

65
Glu Glu Tyr Leu Gln
    Asp     Asp Glu
(Ala$^{63}$ Tyr$^{64}$ Leu/Asp$^{65}$ Glu$^{66}$)
```

DEFINITIONS IN THE INVENTION

The naturally occurring amino acids, with the exception of glycine, contain a chiral carbon atom. Unless otherwise specifically indicated, the optically active amino acids, referred to herein, are of the L-configuration. For example, any of the amino acids of the $A_1$ or $A_{10}$ group can be of the D- or L-configuration. As is customary, the structure of peptides written out herein is such that the amino terminal end is on the left side of the chain and the carboxy terminal end is on the right side of the chain.

An alkyl group and the alkyl portion of an alkoxy group is taken to include straight, branched, or cyclic alkyl groups, for example, methyl, ethyl, propyl, isopropyl, butyl, isobutyl, tert-butyl, pentyl, isopentyl, secpentyl, cyclopentyl, hexyl, isohexyl, cyclohexyl and cyclopentylmethyl, heptyl, octyl(Oct), 8-aminooctanoic acid(Oac). An acyl group of from 2 to 10 carbon atoms is taken to include straight, branched, cyclic, saturated and unsaturated acyl groups having 1 or 2 carbonyl moieties per group, for example, acetyl(Ac), azetidine-2-carboxylate(Azt), benzoyl succinyl, cinnamoyl(Cin), DhCin, maleyl(Mal), and glutaryl(Glt). Both alkyl and acyl substituents are taken to include those groups with halogen substituents, were a halogen group is a fluoro, chloro, bromo or iodo, for example, trifloroacetyl(Tfa).

The term "any amino acid" as used herein does not purport to include any carboxylic acid having an amino substituent, but rather is used as it is commonly used by those skilled in the art of polypeptide derivatives and includes the naturally occurring amino acids as well as other "non-protein" α-amino acids commonly utilized by those in the peptide chemistry arts when preparing synthetic analogs of naturally occurring peptides. The naturally occurring amino acids are the "L-amino acids" glycine, alanine, valine, leucine, isoleucine, serine, methionine, threonine, phenylalanine, tyrosine, tryptophan, cysteine, proline, histidine, aspartic acid, asparagine, glutamic acid, glutamine, arginine, ornithine, and lysine. Also included as "any amino acid" would be the D-amino acids (D-isomers) of the naturally occurring amino acids; D-alanine, D-valine, D-leucine, D-isoleucine, D-serine, D-methionine, D-threonine, D-phenylalanine, D-tyrosine, D-tryptophan, D-cysteine, D-proline, D-histidine, aspartic acid, D-asparagine, D-glutamic acid, D-glutamine, D-arginine. Also included are "non-protein" α-amino acids, examples are norleucine, norvaline, alloisoleucine, homoarginine, thiaproline, dihydroproline, hydroxyproline (Hyp), homoserine, cyclohexylglycine (Chg), α-amino-n-butyric acid (Aba), cyclohexylalanine (Cha), aminophenylbutyric acid (Pba), phenylalanines mono or di-substituted at the ortho, meta, or para positions, such as para substituted phenylalanine (pSubPhe) and para-chloro-phenylalanine, and para-nitrophenylalanine (pNPhe) or positions of the phenyl moiety with one or two of the following, a $(C_1-C_4)$ alkyl, $(C_1-C_4)$ alkoxy, halogen, or nitro groups or substituted with a methylenedioxy group, β-2-, and 3-thienyl-alanine, β-2-and 3-furanylalanine, β-2-,3-, and 4-pyridylalanine, β-(benzothienyl-2- and 3-yl)alanine, β-(1- and 2-naphthyl)alanine(Npa), O-alkylated derivates of serine, threonine, or tyrosine, methyl esters of glutamic and aspartic acid, S-alkylated cysteine, the O-sulfate ester of tyrosine, and halogenated tyrosines such as 3-idodotyrosine, 5-iodotyrosine, 3,5-diiodotyrosine.

The expression "radiolabeled amino acid" includes 3-[$H^3$]-tyrosine, 5-[$H^3$]-tyrosine, 3-[$I^{125}$]-iodotyrosine, 5-[$I^{125}$]-iodotyrosine, 3,5-[$I^{125}$]-diiodotyrosine, 3-[$I^{131}$]-iodotyrosine, 5-[1131-iodotyrosine, and 3,5-[$I^{131}$]-diiodotyrosine. By the expression "sequences of hirudin or its natural variants" applicants intend that the amino acid sequences found for hirudin in nature apply.

The term "portions thereof" when used in regard to hirudin and its variants is meant to include a consecutive region of at least 4 amino acids derived from the sequence of hirudin or its variants.

The term "lipophilic amino acid" includes Tyr, Phe, Leu, Met, Nle, Ile, Val, and Pro. The term "L-aromatic amino acid" is meant to include tyrosine and phenylalanine, and those amino acids containing an aromatic ring.

The expression "a peptide containing from 1-11 residues of any amino acid" is meant to reflect that addition of amino acids to either the amino or carboxy terminal of the "core amino acids ($A_2-A_9$) encompass the core structure with its intrinsic activity.

"Zero to five residues of I-Tyr, [$^3$H]-Tyr, [$^{131}$I]-Tyr [$^{125}$I]-Tyr" is meant to include a sequence containing one to five residues of any amino acid containing I-Tyr, [$^3$H]Tyr, [125I]-Tyr, or [$^{131}$I]-Tyr singularly, multiply, or in combination with any other amino acid. Also included in this definition of I-Tyr, [$^3$H]-Tyr, and [$^{125}$I]-Tyr, [$^{131}$I]-Tyr are the corresponding positional analogs, such as 3-iododotyrosine, 5-iodotyrosine, 3,5-diiodotyrosine, [3-$^3$H]-tyrosine, 5-3H]-tyrosine, [3-$^{125}$I]-iodotyrosine, [5-$^{125}$I]-iodotyrosine, [3,5-di$^{125}$I-diiodotyrosine, [3-$^{131}$I]-Tyrosine, [5-$^{131}$I]-Tyrosine, and 3,5-dii$^{131}$I]-Tyrosine. As an example a sequence containing one to five residues of any amino acid containing I-Tyr, [$^3$H]Tyr, [$^{125}$I]-Tyr, or [$^{131}$I]-Tyr singularly, multiply, or in combination with any other amino acid would be; Suc I-Tyr I-Tyr Glu Pro Ile Pro Glu Glu Ala Cha D-Glu, (example #3; (ID#6) or the insertion of amino acids before, in between, or after the ITyr ITyr dipeptide sequence or any combination thereof.

Other examples of radiolabeled molecules that may be attached to hirudin in accordance with the present invention include radiohalogenated molecules. Radiohalogens useful for diagnostic imaging include but are not limited to, $^{125}$I and $^{123}$I for imaging by scanning the patient with a gamma camera, and $^{18}$F, $^{75}$Br, or $^{76}$Br for positron tomographic imaging.

The polypeptides of formula 1 can form pharmaceutically acceptable salts with any non-toxic, organic or inorganic acid. Illustrative inorganic acids which form suitable salts include hydrochloric, hydrobromic, sulfuric and phosphoric acid and acid metal salts such as sodium monohydrogen orthophosphate and potassium hydrogen sulfate. Illustrative organic acids which form suitable salts include the mono, di and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic and sulfonic acids such as methane sulfonic acid and 2-hydroxyethane sulfonic acid. Salts of the carboxy terminal amino acid moiety include the non-toxic carboxylic acid salts formed with any suitable inorganic or organic bases. Illustratively, these salts include those of alkali metals, as for example, sodium and potassium; alkaline earth metals, such as calcium and magnesium; light metals of Group IIIA including aluminum; and organic primary, secondary and tertiary amines, as for example, trialkylamines, including triethylamine, procaine, dibenzylamine, 1-ethenamine, N,N'-dibenzylethylenediamine, dihydroabietylamine, N-(lower)alkylpiperidine, and any other suitable amine.

As with any generic group of chemical compounds, certain groups are preferred. Applicants prefer those peptide derivatives of formula 1 wherein;

X, is hydrogen, acetyl, or succinyl.

$A_1$, is sequences of hirudin or its natural variants inclusive of amino acids 1 to 54 or regions thereof, or a bond;

$A_2$, is one to five residues of I-Tyr, [$^3$H]-Tyr, [$^{125}$I]-Tyr, [$^{131}$I]-Tyr, or Trp, Glu, His, Leu, Phe, D-Phe, SubPhe, NMePhe, Tha, 3,4-DhCin, Cin, Nap, β-(2- and 3-thienyl)alanine, β-(2-and 3-furanyl)alanine, β-(2-, 3-, and 4-pyridyl)alanine, β-(benzothienyl-2- and 3-yl alanine, or β-(1- and 2-naphthyl)alanine;

$A_3$, is Glu, Ala;

$A_4$, is Glu, Asp, Pro or Ala, Azt, or Pip;

$A_5$, is Ile, Leu;

$A_6$, is Pro, Sar, D-Ala, Hyp or NMePgl;

$A_7$, is Glu, Gln, Asp or Ala;

$A_8$, is Glu, Asp or Ala;

$A_9$, is I-Tyr, [$^3$H]-Tyr, [$^{125}$I]-Tyr, [$^{131}$I]-Tyr, or Tyr, Ala, Pro, Cha, or the dipeptide Ala-Tyr, Tyr-Leu, Ala-Phe, Tyr-Tyr, Ala-Leu, Tyr-Ala, Glu-Leu, D-Tyr-Leu, Leu-Phe, Sar-Cha, Pro-Cha, Cha-Leu, Ala-Cha, Tyr-Cha;

$A_{10}$, is a bond, or YMeGlu, Glu, D-Glu, Asn, D-Asn, Pro, Gln, Ala, Lys, D-Lys, Asp, Orn, Asp, or is Ala; and Y is a carboxy terminal residue selected from OH, ($C_1$–$C_8$) alkoxy, amino, mono or di ($C_1$–$C_4$) alkyl substituted amino acids Especially preferred are those peptide derivatives of formula 1 wherein either;

X is succinyl;
$A_1$ is a bond;
$A_2$ is I-Tyr, [$^3$H]-Tyr, [$^{125}$I]-Tyr, or [$^{131}$I]-Tyr;
$A_3$, is Glu;
$A_4$, is Glu or Pro;
$A_5$, is Ile;
$A_6$, is Pro;
$A_7$, is Glu;
$A_8$, is Glu or Asp;
$A_9$, is Ala-Cha;
$A_{10}$ is YMeGlu, and
Y is OH

SYNTHESIS

The proteins of this invention can be prepared by a variety of procedures readily known to those skilled in the art. Such procedures include solution phase peptide synthesis the solid phase sequential and block synthesis, gene cloning and combinations of these techniques. The solid phase sequential procedure can be performed using established automated methods such as by use of an automated peptide synthesizer. In this procedure, the peptides were constructed on the resin beginning with the C-terminal, protected amino acid. The resin support employed can be any suitable resin conventionally employed in the art for the solid phase preparation of polypeptides, preferably polystyrene which has been crosslinked with 0.5 to about 3 percent divinyl benzene, which has been either chloromethylated or hydroxymethylated to provide sites for ester formation with the initially introduced u-amino protected amino acid. For C-terminal amides a primethylbenzylhydroxylamine resin can be used. After completion of coupling of the sequence either the Boc protecting group was left in place or it was removed and the N-terminal amino group acylated. Displacement of the protected fragment from the resin was accomplished using the appropriate amino alcohol.

An example of a hydroxymethyl resin is described by Bodanszky et al., Chem. Ind. (London) 38, 1597-98 (1966). A chloromethylated resin is commercially available from Bio Rad Laboratories, Richmond, Calif., and the preparation of such a resin is described by Stewart et al., "Solid Phase Peptide Synthesis" (Freeman & Co., San Francisco 1969), Chapter 1, pp. 1-6. The protected amino acid can be bound to the resin by the procedure of Gisin, Helv. Chem Acta, 56, 1476 (1973). Many resin bound, protected amino acids are commercially available. As an example, to prepare a polypeptide of this invention wherein the carboxy terminal end is a γMe-Glu residue, a tert-butyloxycarbonyl (Boc) protected γMeGlu bound to a benzylated, hydroxymethylated phenylacetamidomethyl (PAM) resin can be used.

Following the coupling of the α-amino protected amino acid to the resin support, the protecting group is removed using any suitable procedure such as by using trifluoroacetic acid in methylene chloride, trifluoroacetic acid alone, or HCl in dioxane. The deprotection is carried out at a temperature of between 0° C. and room temperature. Other standard cleaving reagents and conditions for removal of specific α-amino protecting groups may be used. After removal of the α-amino protecting group the other amino protected amino acids are coupled step-wise in the desired order. Alternatively, multiple amino acid groups may be coupled by the solution method prior to coupling with the resin supported amino acid sequence.

The α-amino protecting group employed with each amino acid introduced into the polypeptide sequence may be any such protecting group known to the art. Among the classes of α-amino protecting groups contemplated are (1) acyl type protecting groups such as: formyl, trifluoroacetyl, phthalyl, toluenesulfonyl (tosyl), benzenesulfonyl, nitrophenylsulfenyl, tritylsulfenyl, o-nitrophenoxyacetyl and u.chlorobutyryl; (2) aromatic urethan type protecting groups such as benzyloxycarbonyl and substituted benzyloxycarbonyl, such as p-chlorobenzyloxycarbonyl, p-nitrobenzyl- carbonyl, p-bromobenzyloxycarbonyl, p-methoxybenzyloxycarbonyl, 1-(p-biphenylyl) -1-methylethoxycarbonyl, α,α-dimethyl-3,5-dimethoxybenzyloxycarbonyl and benzhydryloxycarbonyl; (3) aliphatic urethan protecting groups such as tert-butyloxycarbonyl (Boc), diisopropylmethoxycarbonyl, isopropyloxycarbonyl, ethoxycarbonyl and allyloxycarbonyl; (4) cycloalkyl urethan type protecting groups such as cyclopentyloxycarbonyl, adamantyloxycarbonyl and cyclohexyloxycarbonyl; (5) thiourethan type protecting groups such as phenylthiocarbohyl; (6) and alkyl type protecting groups such as triphenylmethyl (trityl) and benzyl; The preferred α-amino protecting group is tert-butyloxycarbonyl.

As is known in the art of solid phase peptide synthesis many of the amino acids bear functionalities requiring protection during the chain preparation. The use and selection of the appropriate protecting group is within the ability of those skilled in the art and will depend upon the amino acid to be protected and the presence of other protected amino acid residues on the peptide. The selection of such a side chain protecting group is critical in that it must be one which is not removed by cleavage during cleavage of the protecting group of the α-amino moiety. For example, suitable side chain protecting groups for lysine are benzyloxycarbonyl and substituted benzyloxycarbonyl, said substituent being selected from halo (e.g., chloro, bromo, fluoro) and nitro (e.g., 2-chlorobenzyloxycarbonyl, p-nitrobenzyloxy-carbonyl, 3,4-dichlorobenzyloxycarbonyl), tosyl, t-amyloxycarbonyl, t-butyloxycarbonyl and diisopropylmethoxycarbonyl. The alcoholic hydroxyl group of threonine and serine can be protected with an acetyl, benzoyl, tert-butyl, trityl, benzyl, 2,6-dichlorobenzyl or benzyloxycarbonyl group. The preferred protecting group is benzyl.

The selection of an appropriate coupling reagent is within the skill of the art. A particularly suitable coupling reagent where the amino acid to be added is Gln, Asn or Arg is N,N'-diisopropylcarbodiimide and 1-hydroxybenzotriazole. The use of these reagents prevents nitrile and lactam formation. Other coupling agents are (1) carbodiimides (e.g., N,N'-dicyclohexylcarbodiimide and N-ethyl-N'-(Y-dimethylaminopropylcarbodiimide); (2) cyanamide (e.g., N,N-dibenzylcyanamide); (3) ketenimines; (4) isoxazolium salts (e.g., N-ethyl-5-phenyl-isoxazolium-3'-sulfonate; (5) monocyclic nitrogen containing heterocyclic amides of aromatic character containing one through four nitrogens in the ring such as imidazolides, pyrazolides, and 1,2,4-triazolides. Specific heterocyclic amides that are useful include N,N'-carbonyldiimidazole and N,N-carbonyl-di-1,2,4-triazole; (6) alkoxylated acetylene (e.g., ethoxyacetylene); (7) reagents which form a mixed anhydride with the carboxyl moiety of the amino acid (e.g., ethylchloroformate and isobutylchloroformate) or the symmetrical anhydride of the amino acid to be coupled (e.g., Boc-Ala-O-Ala-Boc), (8) nitrogen containing heterocyclic compounds having a hydroxy group on one ring nitrogen (e.g., N-hydroxyphthalimide, N-hydroxysuccinimide and 1-hydroxybenzotriazole), and (9) Castro's reagent (BOP). Other activating reagents and their use in peptide coupling are described by Kapoor, *J. Pharm. Sci.*, 59, pp. 1-27 (1970). Applicants prefer the use of the symmetrical anhydride as a coupling reagent for all amino acids except Arg, Asn and Gln.

Each protected amino acid or amino acid sequence is introduced into the solid phase reactor in about a four-fold excess and the coupling is carried out in a medium of dimethylformamide: methylene chloride (1:1) or in dimethylformamide alone or preferably methylene chloride alone. In cases where incomplete coupling occurs, the coupling procedure is repeated before removal of the α-amino protecting group, prior to the coupling of the next amino acid in the solid phase reactor. The success of the coupling reaction at each stage of the synthesis is monitored by the ninhydrin reaction as described by E. Kaiser et al, *Analyt. Biochem.* 34, 595 (1970).

Following the coupling of the α-amino protected amino acid to the resin support, the protecting group is removed using any suitable procedure such as by using trifluoroacetic acid in methylene chloride, trifluoroacetic acid alone, or HCl in dioxane. The deprotection is carried out at a temperature of between 0° C. and room temperature. Other standard cleaving reagents and conditions for removal of specific α-amino protecting groups may be used. After removal of the α-amino protecting group the other amino protected amino acids are coupled step-wise in the desired order. Alternatively, multiple amino acid groups may be coupled by the solution method prior to coupling with the resin supported amino acid sequence.

After the desired amino acid sequence has been obtained, the peptide is removed from the resin and deprotected. This can be done by hydrolysis such as by treatment of the resin bound polypeptide with anhydrous liquid HF in the presence of scavengers (e.g. anisole). Typically protecting group removal is done after the peptide chain synthesis is complete but the protecting groups can be removed at any other appropriate time.

Purification and analysis of the deprotected peptide is accomplished by a number of standard procedures. The selection of the appropriate purification and analysis procedures is within the skill of the art. A suitable purification procedure is preparative HPLC. Analysis of the purified peptides can be done by analytical HPLC, amino acid analysis, fast atom bombardment mass spectrometry, and any other suitable means of analysis.

RADIO-LABELED PEPTIDES

Radio-labeled peptides of the present invention are useful for in vitro and in vivo determinations of thrombin and thrombin complexes in research and therapy, or useful in assay or diagnostic kits of the same, for preparation of the radio-labeled thrombin-binding agents. One embodiment of the invention is the radio-labeling of thrombin binding peptides which also reduce or eliminates the thrombolytic activity of thrombin which may serve to stabilize such complexes. An example of this would be radioimaging of thrombi incorporated into clots. The binding of the labeled hirudin peptide to thrombin would allow the determination of the location and distribution of the thrombi by radioimaging techniques.

Radio-iodination of peptides is generally done using Chloramine T method. Alternate methods to Chloramine T for labeling peptides include; (1) The iodine monochloride method, (2) Alternative chemical oxidation methods, (3) electrolytic iodination, and (4) enzymatic iodination methods. Alternatively (5), conjugation labeling methods for the iodination of proteins and polypeptides is well known by people skilled in the art using N-succinimidyl 3-(4-hydroxy 5-[$^{125}$I]iodophenyl) propionate (Bolton-Hunter reagent) or other suitable labeling method. For example, Methyl p-hydroxybenzimidate hydrochloride has been used as the iodinating reagent as has radioiodinated diazotized anilines. Conversion of iodinated peptides to peptides containing tritium can be accomplished using catalytic reduction with paladium oxide and tritium gas.

THERAPEUTIC USE

The anticoagulant dose of an peptide derivative of this invention is from 0.2 mg/kg to 250 mg/kg of patient body weight per day depending on the patient, the severity of the thrombotic condition to be treated and the peptide derivative selected. The suitable dose for a particular patient can be readily determined. Preferably from 1 to 4 daily doses would be administered typically with from 5 mg to 100 mg of active compound per dose. The amount of a peptide of this invention required to inhibit or prevent blood coagulation in an extracorporeal medium such as stored whole blood can be readily determined by those skilled in the art.

Anticoagulant therapy is indicated for the treatment and prevention of a variety of thrombotic conditions, particularly coronary artery and cerebrovascular disease. Those experienced in this field are readily aware of the circumstances requiring anticoagulant therapy. The term "patient" used herein is taken to mean mammals such as primates, including humans, sheep, horses, cattle, pigs, dogs, cats, rats and mice. Inhibition of blood coagulation is useful not only in anticoagulant therapy of individuals having thrombotic conditions, but is useful whenever inhibition of blood coagulation is desirable, such as to prevent coagulation in stored whole blood and to prevent coagulation in other biological samples for testing or storage.

Although some of the peptide derivatives may survive passage through the gut following oral administration, applicants prefer non-oral administration, for example, subcutaneous, intravenous, intramuscular or intraperitoneal; administration by depot injection; by implant preparation; or by application to the mucous membranes, such as, that of the nose, throat and bronchial tubes, for example, in an aerosol can containing a peptide derivative of this invention in a spray or dry powder form.

For parentral administration the compounds may be administered as injectable dosages of a solution or suspension of the compound in a physiologically acceptable diluent with a pharmaceutical carrier which can be a sterile liquid such as water and oils with or without the addition of a surfactant and other pharmaceutically acceptable adjuvants. Illustrative of oils which can be employed in these preparations are those of petroleum, animal, vegetable, or synthetic origin, for example, peanut oil, soybean oil, and mineral oil. In general, water, saline, aqueous dextrose and related sugar solutions, ethanol and glycols such as propylene glycol or polyethylene glycol are preferred liquid carriers, particularly for injectable solutions.

The compounds can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber manufactured by the Dow-Corning Corporation.

EXAMPLES

This invention is illustrated by the following, nonlimiting examples.

EXAMPLE 1 (ID#4)

SYNTHESIS OF Suc 3,5-diI-Tyr Glu Pro Ile Pro Glu Glu Ala Cha D-Glu (ID#4).

Suc 3,5-diI-Tyr Glu Pro Ile Pro Glu Glu Ala Cha D-Glu was synthesized by solid phase methods with an ABI 430A Peptide synthesizer. Preformed symmetrical anhydrides of Nα-Boc protected amino acids were added sequentially to Boc-glu(Bzl) Merrifield resin (0.34 meq/gm) using double coupling protocols supplied by ABI. The following side chain protection was used: 3,5-diI-Tyr (3-Br-Bzl); Glu (Bzl). Succinylation of the N-terminus of the resin bound peptide was accomplished with succinic anhydride.

The peptide was cleaved from the resin with anhydrous HF @0° C., for 30 min, in presence of anisole. The peptide was extracted with 5% HoAc, H$_2$O, 30% CH$^3$CN and lyophilized. The lyophilizate was purified by Reverse Phase HPLC using a Beckman Ultraprep C-18 column (50.8 × 150mm) @80ml/min with a gradient of 30–40% CH$^3$CN/aqueous TFA.

Direct iodination of hirudin peptides was carried out with Na[$^{125}$I]. Generally 50ug of hirudin Peptide (2mg/ml) in 0.5 M sodium phosphate (pH 7.5) was iodinated by the addition of 10 ul of Chloramine-T (1.25mg/ml in 0.5 M phosphate buffer). This reaction was allowed to proceed for 30 s at 24° C. The reaction was then terminated by the addition of 25 ul of sodium metabisulfite (1.25mg.ml in 0.5 M phosphate buffer). The iodination reaction was immediately applied to a Bio-Gel P-2 column (2.6 x 50 cm) equilibrated with 0.1 M sodium borate buffer, pH 8.5. Approximately 85% of the $^{125}$I molecules was transferred to the protein as determined by column chromatography. The labeled hirudin peptides were then immediately added to 1% bovine serum albumin, 0.1 M sodium borate buffer (1:1), and stored at −20° C. in several vials. A freshly thawed sample of labeled hirudin is then used for each experiment. After storage, re-chromatography of the labeled hirudin peptides on TKS-3000 HPLC Column yielded a single peak of radioactivity which coincided with the elution profile of unlabeled hirudin peptides.

Peptides of hirudin were tritiated by catalytic reduction. Fifteen mg of peptide was suspended in 2ml of H$_2$O and 30 ul of triethylamine. To this solution was added 30 ug of platinum aluminum oxide. Atmospheric reduction was carried out at room temperature for 1 hr. Initially reactions were washed on filters with H$_2$O to remove incorporated label, and the resulting crude material reisolated. (See Dupont-NEN Research Catalog p.22, Cat. #8259, Catalytic Reduction with platinum oxide).

Analysis of purified labeled peptides gave the desired molecular ion peak by FAB-MS and had an amino acid analysis in accordance with the desired peptide. In this way the following peptides have the stated physical properties specified below.

Samples were tested in a thrombin induced fibrin clot inhibition assay. All the solutions of the assay were made with an assay buffer containing 0.12 M sodium chloride, 0.01 M sodium phosphate, 0.01% sodium azide and 0.1% bovine serum albumin, pH 7.4. Bovine thrombin was titrated to an appropriate concentration so that fibrin clot formation could be monitored by a microtiter plate reader (Bio-Tek EL 309) within 60 min at 405 nm. This solution of thrombin (50 ul; 0.2 pmol) was added to the wells of a microtiter plate containing 50 ul of a solution of the synthetic peptide being tested. After 1 min agitation and an additional 10 mins incubation at 24° C., 100 ul of diluted plasma (1:10) in 0.1% EDTA was added and vortexed for 20 s. The turbidity of the solution was monitored by the autoreader at 5 min intervals. IC$_{50}$ is calculated from the results and is defined as the concentration of peptide which lead to 50% of the turbidity observed relative to a control containing no inhibitor. This is equivalent to a twofold increase in fibrin clot formation time. For the assays using human or bovine thrombin, thrombin was titrated to concentrations that gave the fibrin clot at the same rate over a 30 min period. In this way the following peptides have the stated biological properties for the examples specified below were expresses an IC$_{50}$ between 25 μm and 200 μm, and ++; +; expresses an IC$_{50}$ <25 μm, nt expresses "not determined".

| 1) ID #4 |
|---|
| Suc 3,5-diI-Tyr Glu Pro Ile Pro Glu Glu Ala Cha D-Glu MW 1582 FAB-MS (MH)$^+$ 1581 |

| Amino Acid Analysis: | | | | |
|---|---|---|---|---|
| Z(4) | Pro(2) | Ile(1) | Tyr(1) | Ala(1) |
| 4.09 | 1.96 | 0.96 | 0.98 | 0.99 |

In vitro potency: ++

| 2) ID #5 |
|---|
| Suc [$^3$H]-Tyr Glu Pro Ile Pro Glu Glu Ala Cha D-Glu MW 1995 FAB-MS (MH)$^+$ 1996.3 Labeling and analysis contracted to NEN In vitro potency: nt. |

| 3) ID #6 |
|---|
| Suc 3,5-diI-Tyr 3,5-diI-Tyr Glu Pro Ile Pro Glu Glu Ala Cha D-Glu MW 1995 FAB-MS (MH)$^+$ 1996.3 |

| Amino Acid Analysis: | | | | |
|---|---|---|---|---|
| Z(4) | Pro(2) | Ile(1) | Tyr(2) | Ala(1) |
| 4.09 | 1.96 | 0.96 | 1.95 | 0.99 | in vitro potency: ++

In this way the following peptides have been made and characterized with the stated biological properties; for the examples specified below were + signifies an IC$_{50}$>25 uM and <200 μM, and ++ signifies an IC$_{50}$<25 μM. It is expected that the following examples can be directly modified to incorporate a labeled isotope or can be made by adapting the sequence so that it can then incorporate a labeled isotope.

4) ID #7

Suc—Tyr—Pro—Ile—Pro—Glu—Glu—Ala—Cha—D—Glu
MW 1200 FAB-MS (MH)+ 1201

| Z(3) | Pro(2) | Ile(1) | Tyr(1) | Ala(1) |
|------|--------|--------|--------|--------|
| 3.08 | 1.97   | 0.96   | 0.99   | 0.99   |

In vitro potency: +

5) ID #8

H—Gly—Asp—Phe—Glu—Glu—Ile—Glu—Glu—Tyr—Leu—Gln
MW 1370 FAB-MS (MH)+ 1371

| Z(5) | Ile(1) | Tyr(1) | Gly(1) | B(1) | Phe(1) | Leu(1) |
|------|--------|--------|--------|------|--------|--------|
| 4.93 | 0.85   | 0.95   | 1.09   | 1.10 | 1.08   | 0.99   |

In vitro potency: +

6) ID #9

Suc—Tyr—Glu—Pro—Tiq—Glu—Glu—Ala—Cha—D—Glu
MW 1278 FAB-MS (MH)+ 1279

| Z(4) | Pro(1) | Ile(1) | Tyr(1) | Ala(1) | Cha(1) |
|------|--------|--------|--------|--------|--------|
| 4.05 | 0.93   | 0.96   | 0.95   | 1.03   | 1.03   |

In vitro potency: + +

7) ID #10

Suc—Tyr—Glu—Pro—Ile—Pro—Glu—Glu—Ala—Gln—NH₂
MW 1158 FAB-MS (MH)+ 1175

| Z(4) | Pro(2) | Ile(1) | Tyr(1) | Ala(1) |
|------|--------|--------|--------|--------|
| 4.15 | 1.94   | 0.96   | 1.01   | 0.95   |

In vitro potency: + +

8) ID #11

Suc—Tyr—Glu—Pro—Ile—Pro—Glu—Glu—Cha—Gln—NH₂
MW 1256 FAB-MS (MH)+ 1257

| Z(4) | Pro(2) | Ile(1) | Tyr(1) | Ala(1) |
|------|--------|--------|--------|--------|
| 4.15 | 1.98   | 0.91   | 0.97   | 1.05   |

In vitro potency: + +

9) ID #12

Suc—Tyr—Glu—Pro—Ile—Pro—Glu—Ala—Cha—Asn
MW 1184 FAB-MS (MH)+ 1185

| B(1) | Z(2) | Pro(2) | Ile(1) | Tyr(1) | Ala(1) |
|------|------|--------|--------|--------|--------|
| 1.02 | 2.09 | 1.98   | 0.93   | 1.01   | 0.97   |

In vitro potency: + +

10) ID #13

Suc—Tyr—Glu—Pro—Ile—Pro—Glu—Glu—Ala—Asn
MW 1161 FAB-MS (MH)+ 1162

| Z(3) | Pro(2) | Ile(1) | Tyr(1) | Ala(1) | B(1) |
|------|--------|--------|--------|--------|------|
| 3.14 | 1.95   | 0.95   | 1.00   | 0.96   | 1.01 |

In vitro potency: + +

11) ID #14

Mal—Tyr—Pro—Ile—Pro—Glu—Glu—Ala—Cha—D—Glu
MW 1198 FAB-MS (MH)+ 1198

| Z(3) | Pro(2) | Ile(1) | Tyr(1) | Ala(1) |
|------|--------|--------|--------|--------|
| 3.06 | 2.01   | 0.95   | 0.99   | 1.01   |

In vitro potency: +

12) ID #15

Suc—Nap—Pro—Ile—Pro—Glu—Glu—Ala—Cha—D—Glu
MW 1234 FAB-MS (MH)+ 1234

| Z(3) | Pro(2) | Ile(1) | Ala(1) |
|------|--------|--------|--------|
| 3.08 | 2.00   | 0.94   | 0.97   |

In vitro potency: + +

13) ID #16

Suc—Tyr—Glu—Ile—Pro—Glu—Glu—Ala—Cha—D—Glu
MW 1232 FAB-MS (MH)+ 1233

| Z(4) | Pro(1) | Ile(1) | Tyr(1) | Ala(1) |
|------|--------|--------|--------|--------|
| 4.07 | 0.99   | 0.96   | 0.98   | 0.99   |

In vitro potency: +

14) ID #17

Suc—Tyr—Glu—Pro—Pro—Glu—Glu—Ala—Cha—D—Glu
MW 1216 FAB-MS (MH)+ 1217

| Z(4) | Pro(2) | Tyr(1) | Ala(1) |
|------|--------|--------|--------|
| 4.05 | 1.97   | 0.98   | 1.00   |

In vitro potency: +

15) ID #18

Suc—Tyr—Glu—Pro—Ile—Glu—Glu—Ala—Cha—D—Glu
MW 1232 FAB-MS (MH)+ 1233

| Z(4) | Pro(1) | Ile(1) | Tyr(1) | Ala(1) |
|------|--------|--------|--------|--------|
| 4.10 | 1.01   | 0.94   | 0.96   | 0.99   |

In vitro potency: + +

16) ID #19

Suc—Tyr—Glu—Pro—Ile—Pro—Glu—Ala—Cha—D—Glu
MW 1200 FAB-MS (MH)+ 1201

| Z(3) | Pro(2) | Ile(1) | Tyr(1) | Ala(1) |
|------|--------|--------|--------|--------|
| 3.16 | 1.97   | 0.93   | 0.96   | 0.98   |

In vitro potency: + +

17) ID #20

Suc—Tyr—Glu—Pro—Ile—Pro—Glu—Glu—Ala—D—Glu
MW 1176 FAB-MS (MH)+ 1177

| Z(4) | Pro(2) | Ile(1) | Tyr(1) | Ala(1) |
|------|--------|--------|--------|--------|
| 4.08 | 1.97   | 0.96   | 0.99   | 1.00   |

In vitro potency: + +

18) ID #21

Suc—Tyr—Glu—Pro—Ile—Pro—Glu—Glu—Cha—D—Glu
MW 1258 FAB-MS (MH)+ 1259

| Z(4) | Pro(2) | Ile(1) | Tyr(1) |
|------|--------|--------|--------|
| 4.10 | 2.01   | 0.91   | 0.98   |

In vitro potency: + +

19) ID #22

Suc—Tyr—Glu—Pro—Ile—Pro—Glu—Glu—Ala—Gln
MW 1175 FAB-MS (MH)+ 1175

| Z(4) | Pro(2) | Ile(1) | Tyr(1) | Ala(1) |
|------|--------|--------|--------|--------|
| 4.11 | 1.98   | 0.93   | 1.01   | 0.97   |

In vitro potency: + +

20) ID #23

Suc—Phe—Glu—Pro—Ile—Pro—Glu—Glu—Ala—Gln—NH₂
MW 1158 FAB-MS (MH)+ 1159

| Z(4) | Pro(2) | Ile(1) | Ala(1) | Phe(1) |
|------|--------|--------|--------|--------|
| 4.10 | 2.05   | 0.93   | 0.96   | 0.97   |

In vitro potency: +

21) ID #24

Suc—Tyr—Glu—Pro—Ile—Pro—Glu—Glu—Ala—Cha
MW 1200 FAB-MS (MH)+ 1201

| Glx(3) | Pro(2) | Ile(1) | Tyr(1) | Ala(1) |
|--------|--------|--------|--------|--------|
| 3.10   | 1.94   | 0.98   | 0.99   | 0.99   |

In vitro potency: + +

22) ID #25

Suc—Glu—Pro—Ile—Pro—Glu—Glu—Ala—Cha—D—Glu
MW 1166 FAB-MS (MH)+ 1167

| Glx(4) | Pro(2) | Ile(1) | Ala(1) |
|--------|--------|--------|--------|
| 4.12   | 1.95   | 0.96   | 0.98   |

In vitro potency: +

We claim:

1. A radio-labeled peptide derivative of the formula I (ID#26):

(1)X-$A_1$-$A_2$-$A_3$-$A_4$-$A_5$-$A_6$-$A_7$-$A_8$-$A_9$-$A_{10}$-Y wherein;
X is an amino terminal substituent selected from hydrogen, one or two alkyl groups of from 1 to 10 carbon atoms, one or two acyl groups of from 2 to 10 carbon atoms, carbobenzyloxy or t-butyloxy carbonyl;

$A_1$ is a sequence of 1-11 amino acids of hirudin (SEQ ID NO:1), or known naturally occurring amino acid sequence variation of hirudin (SEQ ID NO:2; SEQ ID NO:3), or a bond;

$A_2$ is one to five residues of [$^3$H]-Tyr, [$^{125}$I]-Tyr, [$^{131}$I]-Tyr; unless $A_9$ contains a radio-labeled amino acid then $A_2$ can additionally be I-Tyr, Tyr, or a bond;

$A_3$ is Glu, or Asp;
$A_4$ is Pro, or Glu;
$A_5$ is Ile;
$A_6$ is Tiq, Pro, Hyp, 3,4-dihydroPro, thiazolidine-4-carboxylate, Sar, NMePgl, Azt, or Pip;
$A_7$ is Glu, or Asp;
$A_8$ is Glu, Asdp, or Ala;
$A_9$ is a lipophilic amino acid selected from Tyr, I-Tyr, [$^{125}$I]-Tyr, [$^{131}$I]-Tyr, [$^3$H]-Tyr, Met, Trp, Phe, Leu, Nle, Ile, Val, Cha, His, Ala and Pro or is a dipeptide containing at least one of these amino acids and a amino acid found in hirudin (SEQ ID NO:1), or known naturally occurring amino acid sequence variation of hirudin (SEQ ID NO:2; SEQ ID NO:3);

$A_{10}$ is a sequence of 1-11 amino acids of hirudin (SEQ ID NO:1), or known naturally occurring amino acid sequence variation of hirudin (SEQ ID NO:2; SEQ ID NO:3), D-Glu, Glu, Gln, Asn, or a bond;

Y is a carbonyl substituent (—CO—) of the terminal amino acid selected from OH, ($C_1$-$C_8$) alkoxy, amino, or a mono or di ($C_1$-$C_4$) alkyl substituted amino group; or the terminal substituent to the alpha carbon of the amino acid is an alcohol ($CH_2OH$);

with the proviso that at least 3 amino acids of formula 1 correspond to amino acids present in hirudin (SEQ ID NO:1), or known naturally occurring amino acid sequence variation of hirudin (SEQ ID NO: 2; SEQ ID NO:3).

2. A peptide derivative of claim 1 wherein $A_2$ is I-Tyr, [$^3$H]-Tyr, [$^{131}$I]-Tyr, or [$^{25}$I]-Tyr.
3. A peptide derivative of claim 1 wherein $A_3$ is Glu.
4. A peptide derivative of claim 1 wherein $A_4$ is Pro.
5. A peptide derivative of claim 1 wherein $A_5$ is Ile.
6. A peptide derivative of claim 1 wherein $A_6$ is Pro.
7. A peptide derivative of claim 1 wherein $A_7$ is Glu.
8. A peptide derivative of claim 1 wherein $A_8$ is Glu.
9. A peptide derivative of claim 1 wherein $A_9$ is Ala-Cha.
10. A peptide derivative of claim 1 wherein AID is D-Glu.
11. A peptide derivative of claim 1 wherein X is H.
12. A peptide derivative of claim 1 wherein $A_9$ is I-Tyr, [$^3$H]-Tyr, [$^{125}$I]-Tyr, [$^{131}$I]-Tyr.
13. A peptide derivative of claim 1 having the structure: Suc-[$^{125}$I]-Tyr-Glu-Pro-Ile-Pro-Glu-Glu-Ala-Cha-D-Glu.

14. A peptide derivative of claim 1 having the structure: Suc-[$^3$H]-Tyr-Glu-Pro-Ile-Pro-Glu-Glu-Ala-Cha-D-Glu (ID#5).

15. A peptide derivative of claim 1 having the structure: Suc-[$^{125}$I]-Tyr-[$^{125}$I]-Tyr-Glu-Pro-Ile-Pro-Glu-Glu-Ala-Cha-D-Glu.

16. A method of detecting thrombin in vivo for diagnostic imaging and detecting the pattern of biodistribution of labeled hirudin after administration of an effective amount of a peptide of one of claims 2-12, and 20 in a patient.

* * * * *

UNITED STATES PATENT AND TRADEMARK OFFICE
CERTIFICATE OF CORRECTION

PATENT NO. : 5,279,812
DATED : January 18, 1994
INVENTOR(S) : John L. Krstenansky et al.

Page 1 of 3

It is certified that error appears in the above-identified patent and that said Letters Patent is hereby corrected as shown below:

On title page, item [57] Abstract: The Abstract reads "This invention relates to the usage of anticoagulant peptide derivatives that are iodinated." and should read --This invention relates to novel anticoagulant peptides of hirudin that are capable of being radio-labeled and as such are valuable reagents for the detection of thrombin within the body or appropriate samples thereof as a diagnostic kit.--

At column 1, line 41, the patent reads "from the the" and should read --from the--.

At column 2, line 37, the patent reads "Or di" and should read --or di--.

At column 5, line 2, the patent reads "c-amino" and should read --α-amino--.

At column 5, line 40, the patent reads "[1131-iodotyrosine" and should read --[$I^{131}$]-iodotyrosine--.

At column 5, line 60, the patent reads "[125I]" and should read --[$125_I$]--.

At column 5, line 62, the patent reads "[125I]" and should read --[$125_I$]-- .

At column 7, line 8, the patent reads "[$I^{311}$]" and should read --[$131_I$]--.

At column 7, line 36, the patent reads "u-amino" and should read --α-amino--.

At column 8, line 12, the patent reads "u.chlorobutyryl" and should read --α-chlorobutyryl--.

At column 10, line 24, the patent reads "an peptide" and should read --a peptide--.

Column 11, line 68, the patent reads "incorporated" and should read --unincorporated--.

At column 12, line 33, the patent reads "were expresses" and should read --were +; expresses--.

UNITED STATES PATENT AND TRADEMARK OFFICE
CERTIFICATE OF CORRECTION

PATENT NO.   : 5,279,812
DATED         : January 18, 1994
INVENTOR(S)  : John L. Krstenansky et al.

It is certified that error appears in the above-identified patent and that said Letters Patent is hereby corrected as shown below:

At column 12, line 35, the patent reads "and ++;+; expresses" and should read --and ++; expresses--.
At column 12, line 63, the patent reads "were + signifies" and should read --where + signifies--.
At column 15, the Roman numeral "(ix)" appearing before Sequence Description: SEQ ID NO. 1, should read --(xi)--.
At column 17, item (2)(x)(A), the patent reads "CAZENZVE, J P" and should read --CAZENAVE, J P--
At column 19, (2)(ix)(D) the patent reads "is a D-glutamic" and should read --is D-glutamic--.
At column 19 (2)(ii) the patent reads "MOLECULAR" and should read --MOLECULE--.
At column 21, following the information for SEQ ID NO 7, and before the line Xaa Pro Ile, etc. the following line is missing: --(xi) SEQUENCE DESCRIPTION: SEQ ID NO: 7:--
At column 21, the sequence for No. 7 reads
"Xaa Pro Ile Pro Glu Glu Ala Xaa Xaa"
 15
and should read --Xaa Pro Ile Pro Glu Glu Ala Xaa Xaa--
                  1                 5
At column 23, item (2)(ix)(B) reads "Other Information" and should read --(B) LOCATION: 1--, then --(D) OTHER INFORMATION --
At column 35, item (2)(ix)(D), the patent reads "amino acids of hirudin (ID# Microsoft Corp hirudin(ID# Microsoft Corp" and should read --amino acids of hirudin(ID#1), natural variants of hirudin(ID#2; ID#3), Gly-Asp, or a bond; wherein--.
At column 37, under Modified Site 9, Other Information, the patent reads (twice) "ID#Microsoft Corp" and should read --(ID#1), natural variants of hirudin (ID#2; ID#3)--.

UNITED STATES PATENT AND TRADEMARK OFFICE
CERTIFICATE OF CORRECTION

PATENT NO. : 5,279,812

DATED : January 18, 1994

INVENTOR(S) : John L. Krstenansky et al.

It is certified that error appears in the above-identified patent and that said Letters Patent is hereby corrected as shown below:

At column 37, under Modified Site 10, Other Information, the patent reads "(ID#Microsoft Corp hirudin(ID#Microsoft Corp" and should read --(ID#1) natural variants of hirudin (ID#2; ID#3), D-glu, Glu, Gln, Asn--.
At column 37, under Modified Site 10 (last line) the patent read "variants (ID#Microsoft Corp" and should read --variants (ID#2; ID#3)--.
At column 41, under Modified Site 10, the patent reads "mon or di" and should read --mono or di--.
At column 41, line 60, claim 1, the patent reads "$A_8$ is Glu, Asdp" and should read --$A_8$ is Glu, Asp--.
At column 42, claim 2, line 2, the patent reads "[$^{131}$I-Tyr, or [$^{251}$]-Tyr" and should read --[$^{131}$I]-Tyr, or [$^{125}$I]-Tyr--.
At column 42, claim 10, line 1, the patent reads "wherein AlD is" and should read --wherein $A_{10}$ is--.

Signed and Sealed this

Sixteenth Day of May, 1995

Attest:

BRUCE LEHMAN

Attesting Officer

Commissioner of Patents and Trademarks